ns patent

United States Patent [19]
Abbott et al.

[11] 4,293,490
[45] Oct. 6, 1981

[54] A-30912H NUCLEI

[75] Inventors: Bernard J. Abbott, Greenwood; David S. Fukuda, Brownsburg, both of Ind.

[73] Assignee: Eli Lilly and Company, Indianapolis, Ind.

[21] Appl. No.: 181,443

[22] Filed: Aug. 25, 1980

Related U.S. Application Data

[63] Continuation-in-part of Ser. No. 103,016, Dec. 13, 1979, abandoned.

[51] Int. Cl.$^3$ .................... C07C 103/52; C12P 21/04; H61K 37/00
[52] U.S. Cl. .............................. 260/112.5 K; 435/71; 424/177
[58] Field of Search .................. 435/71; 260/112.5 R; 424/177

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 834289 | 7/1975 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |
| 38-405867 | 7/1963 | Japan | 260/112.5 R |
| 568386 | 4/1972 | Switzerland | 260/112.5 R |

OTHER PUBLICATIONS

T. Kato et al., J. Antibiotics, 29 (12), 1339–1340, (1976).
S. Chihara et al., Agr. Biol. Chem., 37 (11), 2455–2463, (1973).
S. Chihara et al., Ibid., 37 (12), 2709–2717, (1973).
S. Chihara et al., Ibid., 38 (3), 521–529, (1974).
S. Chihara et al., Ibid., 38 (10), 1767–1777, (1974).
T. Suzuki et al., J. Biochem., 56 (4), 335–343, (1964).
J. M. Weber et al., J. Antibiotics 31 (4), 373–374, (1978).
J. Shoji et al., Antibiotics, 28, 764–769, (1975).
J. Shoji et al., Ibid., 29 (4), 380–389, (1976).
J. Shoji et al., Ibid., (12) 1268–1274, (1976).
J. Shoji et al., Ibid., (12) 1275–1280, (1976).
F. Benz et al., Heln. Chim. Acta, 57, 2459, (1974).
C. Keller-Juslen et al., Tetrahedron Letters, 4147–4150, 1976, vol. 46.
R. Traber et al., Helv. Chim. Acta, 62, 1252, (1979).

*Primary Examiner*—Delbert R. Phillips
*Attorney, Agent, or Firm*—Nancy J. Harrison; Arthur R. Whale

[57] ABSTRACT

A-30912H-type nuclei of formula 1, which are prepared by enzymatic deacylation of an antibiotic having formula 2 using an enzyme produced by the Actinoplanaceae, preferably by *Actinoplanes utahensis*. A-30912H-type nuclei and salts thereof are useful intermediates for preparing new semi-synthetic anti-fungal agents.

33 Claims, No Drawings

A-30912H NUCLEI

CROSS-REFERENCE TO RELATED APPLICATION

This application is a continuation-in-part of application Ser. No. 103,016, filed Dec. 13, 1979, now abandoned.

SUMMARY OF THE INVENTION

This invention relates to A-30912H-type nuclei of formula 1:

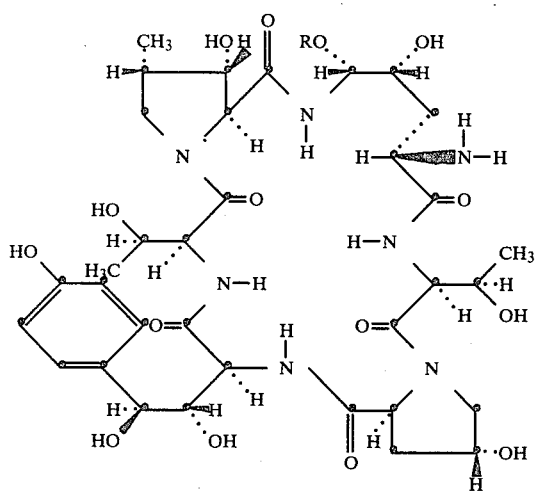

wherein R is $C_1$–$C_6$ alkyl and acid-addition salts thereof. Throughout this application, the cyclic peptide formulas, such as formula 1, assume that the amino acids represented are in the L-configuration. These nuclei and their salts are useful as intermediates in the preparation of semi-synthetic antifungal agents.

In another aspect, this invention relates to a method of deacylating a cyclic peptide antibiotic selected from the group consisting of A-30912 factor H, tetrahydro-A-30912 factor H and lower alkyl ether homologs of A-30912 factor H and tetrahydro-A-30912 factor H. These antibiotics have a cyclic peptide nucleus and a fatty acid side chain. We have discovered a method of enzymatically removing the fatty acid side chain to give the intact cyclic nucleus. For convenience herein, these nuclei will be called A-30912H nuclei. The method comprises exposing the antibiotic in an aqueous medium to an enzyme produced by a microorganism of the family Actinoplanaceae until substantial deacylation is accomplished.

A preferred method of this invention comprises using an enzyme produced by the microorganism *Actinoplanes utahensis* NRRL 12052 to cleave the fatty acid side chain. Deacylation is ordinarily accomplished by adding the appropriate antibiotic to a culture of *A. utahensis* and permitting the culture to incubate until deacylation is accomplished. The A-30912H nucleus thereby obtained is separated from the fermentation broth by methods known in the art. These nuclei are useful in that they can be reacylated to provide new antibiotic substances.

DETAILED DESCRIPTION OF THE INVENTION

1. Field of the Invention

The A-30912H-type nuclei of this invention are obtained by deacylating a peptide antibiotic having structure 2:

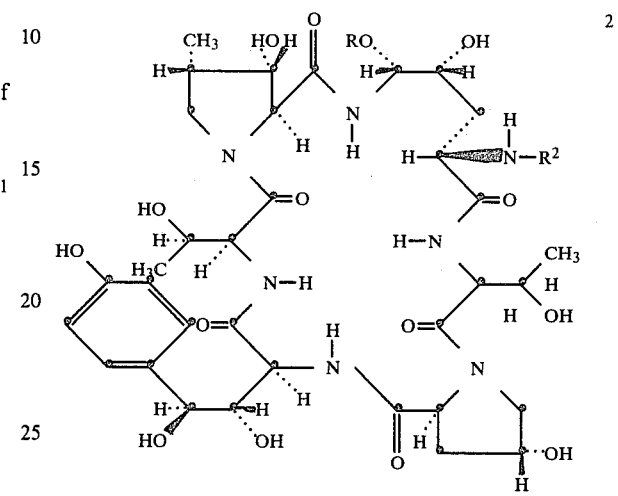

wherein $R^2$ is linoleoyl or stearoyl and R is $C_1$–$C_6$ alkyl. When $R^2$ is linoleoyl and R is methyl, the compound is A-30912 factor H; when $R^2$ is stearoyl and R is methyl, the compound is tetrahydro-A-30912 factor H.

A. A-30912 Factor H

A-30912 factor H is a factor of the A-30912 complex which also contains factors A, C, D, E, F, and G. The A-30912 complex is described by Marvin M. Hoehn and Karl H. Michel in U.S. Pat. No. 4,024,245. A-30912 factor H was a later-discovered A-30912 factor. A-30912 factor H is discussed in a co-pending application of Karl H. Michel entitled ANTIBIOTIC A-30912 FACTOR H, Ser. No. 117,739, filed Feb. 1, 1980, which is a continuation-in-part of application Ser. No. 46,875, filed June 8, 1979 (now abandoned). Another method for preparing A-30912 factor H is described in a co-pending application of LaVerne D. Boeck and Ralph E. Kastner entitled METHOD OF PRODUCING THE A-30912 ANTIBIOTICS, Ser. No. 126,078, filed Mar. 3, 1980, which is a continuation-in-part of application Ser. No. 46,744, filed June 8, 1979 (now abandoned).

B. Homologs of A-30912 Factor H

Following the discovery of the structure of A-30912 factor H, the fact that lower alkyl ($C_2$–$C_6$) ether homologs of A-30912 factor H would be useful products became appreciated. Prior to this time, the ether derivatives which had been prepared were not recognized as having a useful purpose and were prepared only as structure determination tools. The lower alkyl ether homologs of A-30912 factor H are prepared from A-30912 factor A.

A-30912 factor A may be produced by fermentation of: (1) a strain of *Aspergillus rugulosus* NRRL 8113 as described in U.S. Pat. No.4,024,245; (2) a strain of *Aspergillus nidulans* NRRL 8112 as described in U.S. Pat. No. 4,024,246; (3) a strain of *Aspergillus nidulans* var. *echinulatus* A-32204, NRRL 3860 as described in Swiss Pat. No. 568,386; or (4) a strain of *Aspergillus rugulosus* NRRL 8039 as described in Belgian Pat. No. 834,289.

Another method for preparing A-30912 factor A is described in the co-pending Boeck et al. application.

Because each A-30912H nuclei contains an amino moiety, it may exist in the form of salts. Such salts are also useful as intermediates and for purification purposes. The pharmaceutically acceptable salts of the A-30912H nuclei are especially useful because purification of final products will be minimized. "Pharmaceutically acceptable" salts refer to those salts in which the toxicity of product as a whole toward warm-blooded animals is not increased.

Acid addition salts of A-30912H nuclei may be formed by standard reaction procedures with an inorganic or organic acid. Representative inorganic and organic acids include hydrochloric, hydrobromic, hydriodic, sulfuric, phosphoric, acetic, benzoic, sulfamic, tartaric, citric, maleic, succinic, ascorbic, glycolic, lactic, fumaric, palmitic, cholic, pamoic, mucic, D-glutamic, d-camphoric, glutaric, phthalic, lauric, stearic, salicylic, methanesulfonic, benzenesulfonic, sorbic, picric, cinnamic, and other suitable acids.

Preparation of A-30912H Nuclei

A. Preparation of the Substrate

The A-30912H nucleus of this invention, i.e. the compound of formula 1 wherein R is methyl, can be prepared from A-30912 factor H or tetrahydro-A-30912H. Since A-30912 factor H is not a major component of the antibiotic complexes in which it is produced, it should be purified to the extent of removing the other co-produced antibiotic factors before its use as a substrate.

The substrates for the preparation of the A-30912H nuclei of formula 1 wherein R is $C_2$-$C_6$ alkyl (the A-30912H homologs) are prepared by reaction of A-30912 factor A or tetrahydro-A-30912A with an appropriate alcohol to prepare the corresponding $C_2$-$C_6$ ether derivative. Since A-30912 factor A is the major component of the antibiotic complexes in which it is produced, this method is also a preferred way of preparing A-30912 factor H and tetrahydro-A-30912H.

1. A-30912 Factor H

A-30912 factor H may be produced by fermentation of a strain of *Aspergillus rugulosus* NRRL 8113. This organism is described in U.S. Pat. No. 4,024,245. Another method for preparing A-30912 factor H is described in the co-pending application of LaVerne D. Boeck and Ralph E. Kastner. This method uses a new culture which has been named *Aspergillus nidulans* var. *roseus*.

A subculture of this microorganism has been deposited and made a part of the permanent culture collection of the Northern Regional Research Center, U.S. Department of Agriculture, Agricultural Research Culture Collection, North Central Region, Peoria, Illinois 61604, from which it is available to the public under the number NRRL 11440.

When a strain of *A. nidulans* var. *roseus* NRRL 11440 is used to produce A-30912 factor H, a complex of factors is obtained which for convenience is called the A-42355 antibiotic complex. A-30912 factor A is the major factor of the A-42355 antibiotic complex. A-30912 factors B, D and H are minor factors of the A-42355 complex.

As discussed in another co-pending application of Karl H. Michel entitled RECOVERY PROCESS FOR A-30912 ANTIBIOTICS, Ser. No. 103,014, filed Dec. 13, 1979, reversed-phase high performance, low pressure liquid chromatography (HPLPLC) using silica gel/$C_{18}$ adsorbent is a preferred method for the final purification of A-30912 factor H. In this method (see Example 14), A-30912 complex or A-42355 complex (obtained, for example, by extraction of the whole broth or mycelia with methanol and chloroform), dissolved in solvent, is placed on a column equilibrated with the same solvent. The column is then eluted with the solvent. Methanol:water:acetonitrile (7:2:1) is a preferred solvent system. Fractions collected are monitored by *Candida albicans* bioautography and/or by UV (based on relative retention times). Fractions containing A-30912 factor H are combined. It is sometimes necessary to carry out an additional chromatographic separation in order to obtain A-30912 factor H in purified form.

The individual A-30912 factors can be identified by the use of thin-layer chromatography (TLC). Silica gel is a preferred adsorbent.

The $R_f$ values of A-30912 factors A-G, using silica gel (Merck, Darmstadt) TLC, a benzene:methanol (7:3) solvent system, and *Candida albicans* bioautography are given in Table I.

TABLE I

| A-30912 Factor | $R_f$ Value |
| --- | --- |
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table II.

TABLE II

| | $R_f$ Values - Solvent Systems | | | |
| --- | --- | --- | --- | --- |
| A-30912 Factor | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

A-30912 factors A, B, D and H can also be identified by analytical HPLPLC using the following conditions:

| | |
| --- | --- |
| Column: | glass, 0.8 × 15.0 cm |
| Packing: | Nucleosil ® 10-$C_{18}$ (Machery-Nagel and Company); packed using slurry-packing procedure of Example 16 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |

-continued

| Injection: | loop injection |

The approximate retention times for A-30912 factors A, B, D, and H under these conditions are summarized in Table III.

TABLE III

| A-30912 Factor | Retention Time (seconds) |
|---|---|
| A | 792 |
| B | 870 |
| H | 990 |
| D | 1,140 |

2. The A-30912H Homologs

The A-30912H homologs are prepared by reacting A-30912 factor A or tetrahydro-A-30912A with the appropriate corresponding alcohol to form the desired ether derivative of structure 2. This is a preferred method of preparing A-30912 factor H and tetrahydro-A-30912H. The A-30912H homologs of formula 2 wherein $R^2$ is stearoyl and R is $C_2$–$C_6$ alkyl can be prepared by (a) preparing tetrahydro-A-30912A and reacting with the appropriate alcohol to form the ether derivative, or (b) reacting A-30912 factor A with the appropriate alcohol to form the ether derivative and then reducing the double bonds of the linoleoyl side chain.

3. The Tetrahydro Derivatives

Tetrahydro-A-30912A tetrahydro-A-30912H, and the compounds of formula 2 wherein R is $C_2$–$C_6$ and $R^2$ is stearoyl are prepared from A-30912 factors A and H and from the compounds of formula 2 wherein R is $C_2$–$C_6$ and $R^2$ is linoleoyl by standard hydrogenation techniques, carrying out the reduction until both double bonds of the linoleoyl side chain have been reduced.

B. Preparation of the Enzyme

1. The Producing Microorganism

The enzyme which is useful for deacylation of A-30912 factor H, tetrahydro-A-30912H and the A-30912H homologs of formula 2 is produced by certain microorganisms of the family Actinoplanaceae, preferably the microorganism *Actinoplanes utahensis* NRRL 12052.

The enzyme may be the same enzyme which has been used to deacylate penicillins; this work is described by Walter J. Kleinschmidt, Walter E. Wright, Frederick W. Kavanagh, and William M. Stark in U.S. Pat. No. 3,150,059 (issued Sept. 22, 1964). Although a preferred method of cultivating *A. utahensis* NRRL 12052 to produce this enzyme is described in Example 1, it will be recognized by those skilled in the art that other methods may be used.

The Actinoplanaceae are a comparatively recent family of microorganisms of the order Actinomycetales. First described by Dr. John N. Couch, this family was established in 1955 [J. Elisha Mitchell *Sci. Soc.* 71, 148–155 (1955)]. The characteristics of the family and of many individual genera are found in "Bergey's Manual of Determinative Bacteriology", 8th ed., R. E. Buchanan and N. E. Gibbons, Eds., The Williams & Wilkins Co., Baltimore, Md., 1974, pages 706–723. Ten genera have thus far been distinguished: I. Actinoplanes (the type genus and thus far the most common genus); II. Spirillospora; III. Streptosporangium; IV. Amorphosporangium; V. Ampullariella; VI. Pilimelia; VII. Planomonospora; VIII. Planobispora; IX. Dactylosporangium; and X. Kitasatoa.

Some of the species and varieties which have been isolated and characterized so far are: *Actinoplanes philippinensis, Actinoplanes armeniacus, Actinoplanes utahensis,* and *Actinoplanes missouriensis; Spirillospora albida; Streptosporiangium roseum, Streptosporangium vulgare, Streptosporangium roseum* var. *hollandensis, Streptosporangium album, Streptosporangium viridialbum, Amorphosporangium auranticolor, Ampullariella regularis, Ampullariella campanulata, Ampullariella lobata, Ampullariella digitata, Pilimelia terevasa, Pilimelia anulata, Planomonospora parontospora, Planomonospora venezuelensis, Planobispora longispora, Planobispora rosea, Dactylosporangium aurantiacum,* and *Dactylosporangium thailandense.*

The genus Actinoplanes is a preferred source of the enzyme which is useful for this invention. Within the genus Actinoplanes, the species *Actinoplanes utahensis* is an especially preferred source of the enzyme.

Cultures of representative species are available to the public from the Northern Regional Research center, address supra, under the following accession numbers:

*Actinoplanes utahensis:* NRRL 12052
*Actinoplanes missouriensis:* NRRL 12053
Actinoplanes sp.: NRRL 8122
Actinoplanes sp.: NRRL 12065
*Streptosporangium roseum* var. *hollandensis:* NRRL 12064

*A. utahensis* NRRL 12052 was derived from a parent culture which was deposited with the American Type Culture Collection (ATCC), 12301 Parklawn Drive, Rockville, Md. 20852 (*A. utahensis* ATCC 14539). The *A. utahensis* ATCC 14539 culture may also be used as a source of the enzyme.

*A. missouriensis* ARRL 12053 was derived from a culture which was also deposited with ATCC (*A. missouriensis* ATCC 14538) and which is another source of the enzyme.

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. This procedure is described in Sect. E. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. linoleoyl or stearoyl) to restore activity.

2. Conditions for Enzyme Production

Production of the enzyme occurs under conditions satisfactory for growth of the Actinoplanaceae, i.e., a temperature between about 25 and about 30° C. and a pH of between about 5.0 and about 8.0, with agitation and aeration. The culture medium should contain (a) an assimilable carbon source such as sucrose, glucose, glycerol, or the like; (b) a nitrogen source such as peptone, urea, ammonium sulfate, or the like; (c) a phosphate source such as a soluble phosphate salt; and (d) inorganic salts found generally to be effective in promoting the growth of microorganisms. An effective amount of the enzyme is generally obtained in from about 40 to about 60 hours after the beginning of the growth cycle and persists for some time after the effective growth has been reached. The amount of enzyme produced varies from species to species of the organism and in response to different growth conditions.

As will be apparent to those in the field, the microorganisms, such as *Actinoplanes utahensis* NRRL 12052, which produce and enzyme are subject to variation. For example, artificial variants and mutants of these strains may be obtained by treatment with various known mutagens such as ultraviolet rays, X-rays, high-frequency waves, radioactive rays, and chemicals. All natural and artificial variants and mutants which are obtained from the Actinoplanaceae and which produce the enzyme may be used in this invention.

C. Deacylation Conditions

The substrate used as the starting material is preferably added to the culture of Actinoplanaceae after the culture has been incubated for at least about 48 hours. The concentration of substrate in the conversion medium can vary widely. For maximum use of the enzyme and for substantially complete deacylation within a 24-hour period, however, the concentration of substrate will generally range from about 0.5 to about 1.0 mg/ml. Lower concentration can be used, but may not make maximum use of the enzyme; higher concentrations can also be used, but the substrate may not be completely deacylated unless the fermentation time is extended.

Conversion of the substrate to the corresponding A-30912H nucleus according to this invention proceeds best when the pH of the fermentation medium is maintained in the range of from about 6.0 to about 7.0. A pH of about 6.5 is preferred.

After addition of the substrate, incubation of the culture should be continued for about 24 hours or longer. The purity of the substrate will affect the rate of deacylation. When substrates of lower purity are used, the deacylation proceeds at a slower rate. Multiple substrate feedings may be made.

The deacylation can be carried out over a broad temperature range, e.g. from about 20° to about 45° C. It is preferable, however, to carry out the deacylation at temperatures of from about 25° to about 30° C., especially at about 26° C., for optimum deacylation and stability of substrate and nucleus.

D. The Substrate

It is preferable to use purified antibiotic as the substrate. The substrate antibiotics have antifungal, but no antibacterial, activity. Thus, the substrate materials may harbor bacterial cells or spores which could grow in the deacylation fermentation medium. Such contaminants can affect the deacylation reaction or the stability of the starting antibiotic or the product nucleus. It is important, therefore, that the substrates be sterile. Since autoclaving destroys most of the substrate antibiotic, it is preferable to sterilize preparations with ethylene oxide treatment in a pressurized system.

E. Monitoring the Deacylation

The starting materials are antifungal antibiotics which are especially active against *Candida albicans*. For this reason an assay using *C. albicans* is preferable for determining quantities of substrate present. The A-30912H-type nucleus which is formed is water soluble, but is biologically inactive. Reduction in biological activity is, therefore, a quick, presumptive test for deacylation. Both broth samples and alcoholic extracts of the fermentation solids must be assayed because the substrate is only slightly soluble in the broth.

F. Use of Resting Cells

An alternate method of deacylation involves removing the Actinoplanaceae cells from the culture medium, resuspending the cells in a buffer solution, and carrying out the deacylation as described in Sect. C. When this method is used, the enzymatically active mycelia can be re-used. For example, *A. utahensis* NRRL 12052 mycelia retain deacylase activity after storage for one month or longer under refrigeration (4°–8° C.) or in the frozen state (−20° C.). A preferred buffer solution is 0.1 molar phosphate buffer.

G. Immobilized Enzymes

Yet another method of carrying out the deacylation is to immobilize the enzyme by methods known in the art. (See, for example, "Biomedical Applications of Immobilized Enzymes and Proteins", Thomas Ming Swi Chang, Ed., Plenum Press, New York, 1977; Vol. 1.) The immobilized enzyme can then be used in a column (or other suitable type of reactor) to effect the deacylation.

In addition, the microorganism itself can be immobilized and used to catalyze the deacylation reaction.

Utility of the A-30712H Nuclei

The A-30912H-type nuclei and their acid-addition salts are useful intermediates in the preparation of synthetic antifungal compounds. Useful antifungal compounds prepared from these nuclei are described in a co-pending application of Bernard J. Abbott and David S. Fukuda Ser. No. 103,316) and of two co-pending applications of Manuel Debono Ser. No. 103,147, and Ser. No. 103,146) all of which are entitled DERIVATIVES OF A-30912H NUCLEUS and which were filed Dec. 13, 1979. Continuation-in-part application of these applications, with the corresponding Ser. Nos. 181,451, 182,248, and 181,034 are being filed herewith this even date.

The compounds described in the Abbott and Fukuda application have the general formula shown in structure 3:

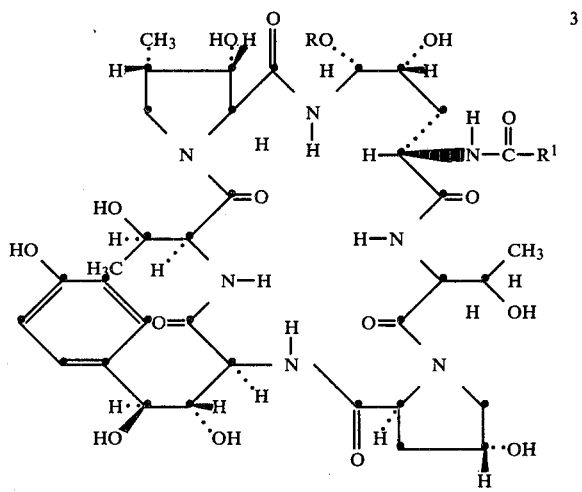

wherein R is $C_1$–$C_6$ alkyl and $R^1$ is $C_6$–$C_{24}$ alkyl or $C_6$–$C_{24}$ alkenyl; provided that, when R is methyl and $R^1$ is alkyl, it cannot be n-heptadecyl; and, when R is methyl and $R^1$ is alkenyl, it cannot be cis,cis-8,11-heptadecadienyl.

The term "alkyl" means a univalent, saturated, straight-chain or branched-chain hydrocarbon radical. The term "alkenyl" means a univalent, unsaturated, straight-chain or branched-chain hydrocarbon radical containing not more than three double bonds. The double bonds of the unsaturated hydrocarbon chain may be either in the cis or trans configuration. By "$C_6$–$C_{24}$" is meant a hydrocarbon (including straight and branched chains) containing from 6 to 24 carbon atoms.

The following are preferred embodiments of the compounds of formula 3:

(a) compounds wherein $R^1$ is alkyl of the formula $CH_3(CH_2)_n$-, wherein n is an integer from 5 to 23, provided that n cannot be 12, 13, 14, or 16;

(b) compounds wherein $R^1$ is alkyl of the formula $CH_3(CH_2)_n$-, wherein n is 10, 11, 15, 17, 18, 19, or 20;

(c) compounds wherein $R^1$ is alkyl of the formula

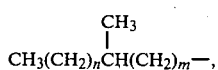

wherein n and m are each independently an integer from 0 to 21 provided that n+m must be no less than 3 and no greater than 21;

(d) compounds wherein $R^1$ is alkenyl containing one cis or trans double bond;

(e) compounds wherein $R^1$ is cis or trans alkenyl of the formula

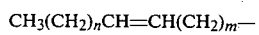

wherein n and m are each independently an integer from 0 to 21, provided that n+m must be no less than 3 and no greater than 21;

(f) compounds wherein $R^1$ is alkenyl containing two cis or trans double bonds;

(g) compounds wherein $R^1$ is cis or trans alkenyl of the formula

wherein n and p are each, independently, an integer of from 0 to 18 and m is an integer of from 1 to 19, provided that m+n+p must be no less than 1 and no greater than 19 and that $R^1$ cannot be linoleoyl; and (h) the compounds wherein $R^1$ is:
cis-$CH_3(CH_2)_5CH=CH(CH_2)_7$-
trans-$CH_3(CH_2)_5CH=CH(CH_2)_7$-
cis-$CH_3(CH_2)_{10}CH=CH(CH_2)_4$-
trans-$CH_3(CH_2)_{10}CH=CH(CH_2)_4$-
cis-$CH_3(CH_2)_7CH=CH(CH_2)_7$-
trans-$CH_3(CH_2)_7CH=CH(CH_2)_7$-
cis-$CH_3(CH_2)_5CH=CH(CH_2)_9$-
trans-$CH_3(CH_2)_5CH=CH(CH_2)_9$-
cis-$CH_3(CH_2)_7CH=CH(CH_2)_9$-
trans-$CH_3(CH_2)_7CH=CH(CH_2)_9$-
cis-$CH_3(CH_2)_7CH=CH(CH_2)_{11}$-
trans-$CH_3(CH_2)_7CH=CH(CH_2)_{11}$-
trans,trans-$CH_3(CH_2)_4CH=CHCH_2CH=CH(CH_2)_7$-
cis,cis,cis-$CH_3CH_2CH=CHCH_2CH=CHCH_2CH=CH(CH_2)_7$-
n-tridecyl
n-tetradecyl
n-pentadecyl

The Debono Derivatives

The compounds of the two Debono applications have the chemical structure depicted in formula 4:

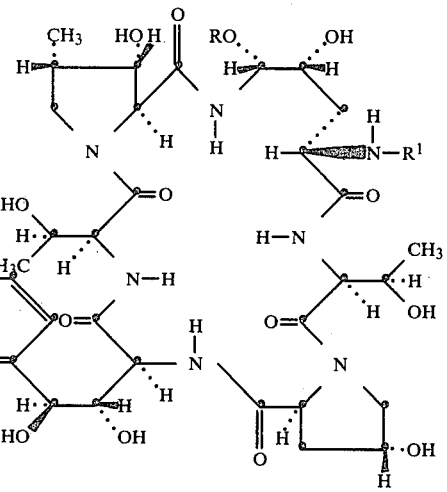

wherein R is $C_1$–$C_6$ alkyl.

A. Debono Group I

In the group of derivatives described in Debono application Serial No. 103,147, Docket No. X-5518 (Debono Group I), $R^1$ is an N-alkanoyl amino acyl group of the formula (

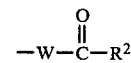

wherein:

W is a divalent aminoacyl radical of the formula:

(a) 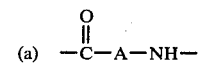

wherein A is $C_1$–$C_{10}$ alkylene or $C_5$–$C_6$ cycloalkylene;

(b) 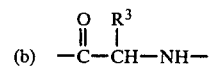

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$ alkylthio, carbamoyl, or $C_1$–$C_3$ alkylcarbamoyl;

(c) 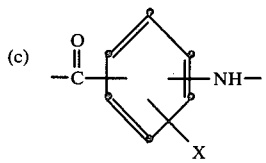

wherein X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamoyl, or $C_1$–$C_3$ alkylcarbamoyl;

(d) 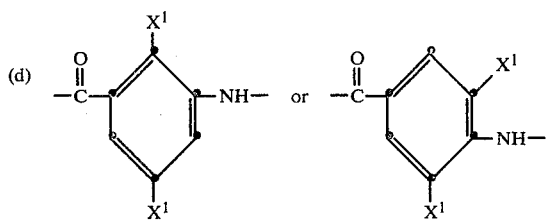

wherein X¹ is chloro, bromo, or iodo;

(e) 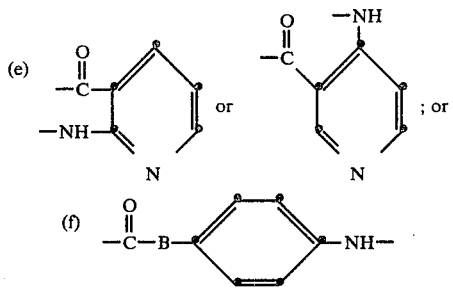 ; or (f) 

wherein B is a divalent radical of the formula: —(CH$_2$)$_n$—, wherein n is an integer from 1 to 3; —CH=CH—; —CH=CH—CH$_2$—; or

and R$^2$ is C$_1$-C$_{17}$ alkyl or C$_2$-C$_{17}$ alkenyl.

The terms "alkylene", "alkyl", "alkoxy", "alkylthio", and "alkenyl" after to both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative, preferred C$_1$-C$_{10}$ alkylene radicals are: —CH$_2$—;

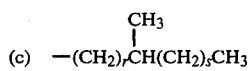

in which R$^5$ is C$_1$-C$_4$ alkyl (i.e., methyl, ethyl, n-propyl, isopropyl, n-butyl, tert-butyl, isobutyl, or 1-methylpropyl); —(CH$_2$)$_m$— in which m is an integer from 2 to 10, and CH$_3$—(CH$_2$)$_q$—CH—(CH$_2$)$_p$—, in which p is an integer from 1 to 8 and q is an integer from 0 to 7, provided that n+m must be no greater than 8.

Illustrative, preferred C$_1$-C$_{17}$ alkyl groups are:
(a) CH$_3$—;
(b) —(CH$_2$)$_n$CH$_3$ wherein n is an integer from 1 to 16; and (c) —(CH$_2$)$_r$CH(CH$_3$)(CH$_2$)$_s$CH$_3$ wherein r and s are independently an integer from 0 to 14 provided that r+s can be no greater than 14.

Illustrative, preferred C$_2$-C$_{17}$ alkenyl radicals are:

(a) —(CH$_2$)$_t$—CH=CH—(CH$_2$)$_u$—CH$_3$ wherein t and u are independently an integer from 0 to 14 provided that t+u can be no greater than 14; and (b) —(CH$_2$)$_v$—CH=CH—(CH$_2$)$_y$—CH=CH—(CH$_2$)$_z$—CH$_3$ wherein v and z are independently an integer from 0 to 11 and y is an integer from 1 to 12 provided that v+y+z can be no greater than 11.

In particular, the following C$_1$-C$_{17}$ alkyl groups are preferred:
CH$_3$—
CH$_3$(CH$_2$)$_5$—
CH$_3$(CH$_2$)$_6$—
CH$_3$(CH$_2$)$_8$—
CH$_3$(CH$_2$)$_{10}$—
CH$_3$(CH$_2$)$_{12}$—
CH$_3$(CH$_2$)$_{14}$—
CH$_3$(CH$_2$)$_{16}$—

The following C$_2$-C$_{17}$ alkyl groups are especially preferred:
cis-CH$_3$(CH$_2$)$_5$CH=CH(CH$_2$)$_7$-
trans-CH$_3$(CH$_2$)$_5$CH=CH(CH$_2$)$_7$-
cis-CH$_3$(CH$_2$)$_{10}$CH=CH(CH$_2$)$_4$-
trans-CH$_3$(CH$_2$)$_{10}$CH=CH(CH$_2$)$_4$-
cis-CH$_3$(CH$_2$)$_7$CH=CH(CH$_2$)$_7$-
trans-CH$_3$(CH$_2$)$_7$CH=CH(CH$_2$)$_7$-
cis-CH$_3$(CH$_2$)$_5$CH=CH(CH$_2$)$_9$-
trans-CH$_3$(CH$_2$)$_5$CH=CH(CH$_2$)$_9$-
cis,cis-CH$_3$(CH$_2$)$_4$CH=CHCH$_2$CH=CH(CH$_2$)$_7$-
trans,trans-CH$_3$(CH$_2$)$_4$CH=CHCH$_2$CH=CH(CH$_2$)$_7$-
cis,cis,cis-CH$_3$CH$_2$CH=CHCH$_2$CH=CHCH$_2$CH=CH—(CH$_2$)$_7$-.

When "W" is a divalent radical of the formula

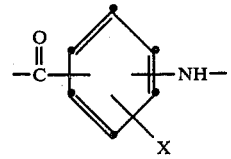

a preferred embodiment is that in which X is hydrogen and the

and —NH— functions are oriented in the para configuration.

The terms "substituted phenyl" and "substituted benzyl", as defined by R$^3$ in formula 5, contemplate substitution of a group at any of the available positions in the benzene ring—i.e. the substituent may be in the ortho, meta, or para configuration.

The term "C$_1$-C$_3$ alkyl", as defined by R$^3$ or X in formula 5, includes the methyl, ethyl, n-propyl, or isopropyl groups.

B. Debono Group II

In the group of derivatives of structure 4 described in Debono application Ser. No. 103,146, (Debono Group II), R$^1$ is a substituted benzoyl group of the formula 5:

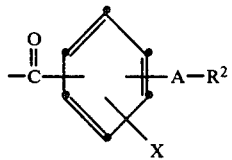

wherein A is divalent oxygen, sulfur, sulfinyl, or sulfonyl; X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamoyl, or $C_1$-$C_3$ alkylcarbamoyl; and $R^2$ is $C_5$-$C_{18}$ alkyl or $C_5$-$C_{18}$ alkenyl.

In the substituted benzoyl group ($R^1$), the

function and the —$AR^2$ function may be oriented on the benzene ring in the ortho, meta, or para position relative to each other. The para orientation is preferred. The substituent represented by X may be substituted at any available position of the benzene ring not occupied by the

and $AR^2$ groups.

The terms "alkyl" and "alkenyl" are as defined in the Group I derivatives.

Illustrative, preferred $C_5$-$C_8$ alkyl radicals are:

(a) —$(CH_2)_n CH_3$ wherein n is an integer from 4 to 17, and

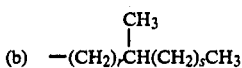

wherein r and s are, independently, an integer from 0 to 15, provided that r+s can be no greater than 15 or no less than 2.

Illustrative, preferred $C_5$-$C_{18}$ alkenyl radicals are:

(a) —$(CH_2)_t$—CH=CH—$(CH_2)_n$—$CH_3$ wherein t is an integer from 1 to 15, and n is an integer from 0 to 15 provided that t+n can be no greater than 15 or no less than 2; and (b) —$(CH_2)_v$—CH=CH—$(CH_2)_y$—CH=CH—$(CH_2)_z$—$CH_3$ wherein v and z are, independently, an integer from 0 to 12 and y is an integer from 1 to 13 provided that v+y+z must be no greater than 13.

PREPARATION OF THE DERIVATIVES

The compounds of formulas 3 and 4 are prepared by acylating the A-30912H-type nucleus at the amino group of the nucleus with the appropriate acyl side chain using methods conventional in the art for forming an amide bond. The acylation is accomplished, in general, by reacting the A-30912H-type nucleus with an activated derivative of the acid corresponding to the desired acyl side chain group.

The term "activated derivative" means a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride or aryloxyformic acid anhydride) or (c) an activated ester (e.g. a 2,4,5-trichlorophenyl ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of formulas 3 and 4 is by the active ester method. The use of the 2,4,5-trichlorophenyl ester of the desired acid as the acylating agent is most preferred. In this method, an excess amount of the active ester is reacted with the nucleus at room temperature in a non-reactive organic solvent such as dimethylformamide (DMF). The reaction time is not critical, although a time of about 15 to about 18 hours is preferred. At the conclusion of the reaction, the solvent is removed, and the residue is purified by a recognized method, such as by column chromatography. Chromatography using silica gel as the stationary phase and ethyl acetate:methanol (3:2) as the solvent system is a preferred method.

The 2,4,5-trichlorophenyl esters of the corresponding acids can be prepared conveniently by treating the desired acid with 2,4,5-trichlorophenol in the presence of a coupling agent, such as N,N'-dicyclohexylcarbodiimide. Other methods suitable for preparing acid esters will be apparent to those skilled in the art.

The alkanoic and alkenoic acids used as starting materials for the Abbott and Fukuda derivatives of formula 3 and the activated derivatives thereof (in particular, the acid chlorides and the 2,4,5-trichlorophenyl esters), are known compounds and can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide. The 2,4,5-trichlorophenyl ester derivative can be purified by column chromatography over silica gel in toluene.

The N-alkanoylamino acids or N-alkenoylamino acids used as starting materials for the Debono Group I derivatives of formula 4 are either known compounds or they can be made by acylating the appropriate amino acid with the appropriate alkanoyl or alkenoyl group using conventional methods. A preferred way of preparing the N-alkanoylamino acids is by treating the appropriate amino acid with an alkanoic acid chloride in pyridine. The alkanoic acids, the activated derivatives thereof, and the amino acids used are either known compounds or they can be made known by methods or by modification of known methods which will be apparent to those skilled in the art.

If a particular amino acid contains an acylable functional group other than the amino group, it will be understood by those skilled in the art that such a group must be protected prior to reaction of the amino acid with the reagent used to attach the N-alkanoyl or N-alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids used in the synthesis of these products may exist in optically active forms. Both the natural configuration (L-configuration) and unnatural configuration (D-configuration) may be used as starting materials.

The substituted benzoic acids used as starting materials for the Debono II derivatives and the activated derivatives thereof are either known compounds or they can be made from known compounds by methods known in the art. The alkoxybenzoic acids or alkenyloxybenzoic acids can be prepared conveniently from an appropriate hydroxybenzoic acid by reacting an appropriate alkyl or alkenyl halide with the disodium salt of the appropriate hydroxybenzoic acid. The (alkylthio)benzoic acids or the (alkenylthio)benzoic acids can be prepared conveniently by treating the appropriate substituted S-(4-carbomethoxyphenyl)dimethylthiocarbamate of the general formula

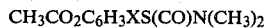

with aqueous sodium hydroxide at 65°–85° C., then adding the appropriate alkyl or alkenyl bromide, and continuing heating for 2-4 hours. The substituted S-(4-carbomethoxyphenyl)dimethylthiocarbamates can be made from the appropriate hydroxybenzoic acids by the method of M. Newman and H. Kanes, *J. Org. Chem.* 31, 3980 (1966).

When it is desired to prepare a Debono II derivative of formula 4 wherein A is sulfinyl or sulfonyl, the appropriate sulfoxide or sulfone derivative of the (alkenylthio)- or (alkylthio)benzoic acid (formula 5) can be used for acylation of the nucleus. The appropriate sulfoxides or sulfones can be made by oxidation of the corresponding thioether compound using conventional agents, such as m-chloroperbenzoic acid, tert-butyl hypochlorite, sodium metaperiodate, or hydrogen peroxide. If a double bond is present in the thioether, very mild conditions should be used to avoid epoxidation. If equimolar amounts of reactants are taken, the product is a sulfoxide (A is sulfinyl), which is readily oxidized to the sulfone (A is sulfonyl) by an additional mole of the oxidizing agent.

The hydroxybenzoic acids and substituted derivatives thereof used as starting materials in the processes described herein are either known compounds or can be prepared by conventional methods which are known in the art.

UTILITY OF THE DERIVATIVES

The compounds of formulas 3 and 4 inhibit the growth of pathogenic fungi and are useful, therefore, for controlling the growth of fungi on environmental surfaces (as an antiseptic) or in treating infections caused by fungi. In particular, the compounds are active against *Candida albicans* and are, thus, especially useful for treating candidosis. The activity of the compounds can be assessed in standard microbiological test procedures, such as in vitro in agar-plate disc-diffusion tests or in agar-dilution tests, or in vivo in tests in mice infected with *C. albicans*. The compounds are also active against *Trichophyton mentagrophytes* (a dermatophytic organism), *Saccharomyces pastorianus*, and *Neurospora crassa*.

When employed systemically, the dosage of the compounds of formulas 3 and 4 will vary according to the particular compound being employed, the severity and nature of the infection, and the physical conditions of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose, may be added to make the solutions isotonic. The proportions and nature of such additives will be apparent to those skilled in the art.

When used to treat vaginal Candida infections, the compounds of formulas 3 and 4 can be administered in combination with pharmaceutically acceptable conventional excipients suitable for intravaginal use. Formulations adapted for intravaginal administration will be known to those skilled in the art.

In order to illustrate the operation of this invention more fully, the following examples are provided.

EXAMPLE 1

Preparation of A-30912H Nucleus

A-30912H Nucleus

A-30912H nucleus, i.e., the compound of formula 1 wherein R is methyl, is prepared by the following procedure:

A. Fermentation of *Actinoplanes utahensis*

A stock culture of *Actinoplanes utahensis* NRRL 12052 is prepared and maintained on an agar slant. The medium used to prepare the slant is selected from one of the following:

| MEDIUM A | |
| --- | --- |
| Ingredient | Amount |
| Pre-cooked oatmeal | 60.0 g |
| Yeast | 2.5 g |
| K$_2$HPO$_4$ | 1.0 g |
| Czapek's mineral stock* | 5.0 ml |
| Agar | 25.0 g |
| Deionized water | q.s. to 1 liter |

*Czapek's mineral stock has the following composition:

| Ingredient | Amount |
| --- | --- |
| FeSO$_4$ . 7H$_2$O (dissolved in 2 ml conc HCl) | 2 g |
| KCl | 100 g |
| MgSO$_4$ . 7H$_2$O | 100 g |
| Deionized water | q.s. to 1 liter |

| MEDIUM B | |
| --- | --- |
| Ingredient | Amount |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| MgSO$_4$ . 7H$_2$O | 0.25 g |

MEDIUM B -continued

| Ingredient | Amount |
| --- | --- |
| CaCO$_3$ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
| --- | --- |
| Pre-cooked oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 liter |
| adjust to pH 7.4 with NaOH; after autoclaving, pH is about 6.8. | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose sodium [see W. A. Dailey and C. E. Higgens, "Preservation and Storage of Microorganisms in the Gas Phase of Liquid Nitrogen", *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
| --- | --- |
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |

MEDIUM I -continued

| Ingredient | Amount (g/L) |
| --- | --- |
| MgSO$_4$ . 7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
| --- | --- |
| Ingredient | Amount (g/L) |
| Sucrose | 30.0 |
| Peptone | 5.0 |
| K$_2$HPO$_4$ | 1.0 |
| KCl | 0.5 |
| MgSO$_4$ . 7H$_2$O | 0.5 |
| FeSO$_4$ . 7H$_2$O | 0.002 |
| Deionized water | q.s. to 1 liter |

Adjust to pH 7.0 with HCl; after autoclaving, pH is about 7.0.

| MEDIUM III | |
| --- | --- |
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$ . 6H$_2$O | 0.304 |
| FeCl$_3$ . 6H$_2$O | 0.062 |
| MnCl$_2$ . 4H$_2$O | 0.035 |
| CuCl$_2$ . 2H$_2$O | 0.005 |
| CaCO$_3$ | 6.0 |
| KH$_2$PO$_4$* | 0.67 |
| Tap water | q.s. to 1 liter |

*Sterilized separately and added aseptically
Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of A-30912 Factor H

A fermentation of *A. utahensis* is carried out as described in Sect. A, using production medium I. After the culture is incubated for about 48 hours, A-30912 factor H, dissolved in a small amount of methanol, is added to the fermentation medium.

Deacylation of A-30912 factor H is monitored by paper-disc assay against *Candida albicans* or *Neurospora crassa*. The fermentation is allowed to continue until deacylation is complete as indicated by disappearance of activity.

C. Isolation of A-30912H Nucleus

Whole fermentation broth, obtained as described in Sect. B, is filtered. The mycelial cake is discarded. The clear filtrate thus obtained is passed through a column containing HP-20 resin (DIAION High Porous Polymer, HP-Series, Mitsubishi Chemical Industries Limited, Tokyo, Japan). The effluent thus obtained is discarded. The column is then washed with up to eight column volumes of deionized water at pH 6.5–7.5 to remove residual filtered broth. This wash water is discarded. The column is then eluted with a water:methanol (7:3) solution. Elution is monitored using the following procedure: Two aliquots are taken from each eluted fraction. One of the aliquots is concentrated to a small volume and is treated with an acid chloride such as myristoyl chloride, using a procedure such as the one described in Example 18. This product and the other (untreated) aliquot are assayed for activity against *Candida albicans*. If the untreated aliquot does not have activity and the acylated aliquot does have activity, the fraction contains A-30912H nucleus. The eluate containing A-30912H nucleus is concentrated under vacuum to a small volume and lyophilized to give crude nucleus.

D. Purification of A-30912H Nucleus by Reversed-Phase Liquid Chromatography

Crude A-30912H nucleus, obtained as described in Section C, is dissolved in water:acetonitrile:acetic acid:pyridine (96:2:1:1). This solution is chromatographed on a column filled with Lichroprep RP-18, particle size 25-40 microns (MC/B Manufacturing Chemists, Inc. E/M, Cincinnati, Ohio). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Nebr. 68504) with an optical unit (ISCO Type 6).

On the basis of absorption at 280 nm, fractions containing A-30912H nucleus are combined, evaporated under vacuum and lyophilized to give purified A-30912H nucleus.

EXAMPLE 2

A-30912H nucleus is prepared and purified by the method of Example 1 except that tetrahydro-A-30912H is used as the substrate.

EXAMPLE 3

A-30912H nucleus is prepared and purified by the method of Example 1 except that A-30912 factor H is prepared from A-30912 factor A using the following procedure:

Antibiotic A-30912 factor A (19.6 mg) is dissolved in dimethylformamide (1 ml). Acidic methanol (3% HCl, 0.06 ml) is added to this solution. The resulting solution is stirred at room temperature overnight and then is evaporated to dryness under vacuum. The residue obtained is chromatographed by HPLPLC as described in Example 14, using reversed-phase silica gel (LP-1/$C_{18}$, prepared as described in Example 15) and $CH_3OH$:$H_2O$:$CH_3CN$ (7:2:1) as the eluting solvent to give 1.4 mg of A-30912 factor H (the compound of formula 2 wherein R is methyl and $R^2$ is linoleoyl).

EXAMPLE 4

The A-30912H-type nucleus of structure 1 wherein R is ethyl is prepared and purified by the method of Example 1, except that the compound of formula 2 wherein R is ethyl and $R^2$ is linoleoyl is used as the substrate. The substrate is prepared by the procedure used in Example 3.

EXAMPLE 5

The A-30912H-type nucleus having structure 1 wherein R is n-propyl is prepared and purified by the method of Example 1, except that the compound of formula 2 wherein R is n-propyl and $R^2$ is linoleoyl is used at the substrate. The substrate is prepared as described in Example 3.

EXAMPLE 6

The A-30912H nucleus having structure 1 wherein R is isobutyl is prepared and purified by the method of Example 1, except that the compound of formula 2 wherein R is isobutyl and $R^2$ is linoleoyl is used as the substrate.

EXAMPLE 7

The A-30912H nucleus of structure 1 wherein R is n-pentyl is prepared and purified by the method of Example 1, except that the compound of formula 2 wherein R is n-pentyl and $R^2$ is linoleoyl is used as the substrate.

EXAMPLE 8

The A-30912H-type nucleus of structure 1 wherein R is n-hexyl is prepared and purified by the method of Example 1, except that the compound of formula 2 wherein R is n-hexyl and $R^2$ is linoleoyl is used as the substrate.

EXAMPLE 9

The A-30912H-type nucleus having structure 1 wherein R is ethyl is prepared and purified by the method of Example 1, except that the compound having formula 2 wherein R is ethyl and $R^2$ is stearoyl is used as the substrate.

EXAMPLE 10

The A-30912H-type nucleus having structure 1 wherein R is 2-ethyl-1-butyl is prepared and purified by the method of Example 1, except that the compound of formula 2 wherein R is 2-ethyl-1-butyl and $R^2$ is linoleoyl is used as the substrate.

EXAMPLE 11

The A-30912H-type nucleus having structure 1 wherein R is 3-methyl-1-butyl is prepared and purified by the method of Example 1, except that the compound of formula 2 wherein R is 3-methyl-1-butyl and $R^2$ is linoleoyl is used as the substrate.

EXAMPLE 12

Preparation of the A-42355 Antibiotic Complex

A. Shake-Flask Fermentation

A culture of *Aspergillus nidulans* var. *roseus* NRRL 11440 is prepared and maintained on an agar slant prepared with medium having the following composition:

| Ingredient | Amount |
| --- | --- |
| Glucose | 5 g |
| Yeast extract | 2 g |
| $CaCO_3$ | 3 g |
| Vegetable juice* | 200 ml |
| Agar** | 20 g |
| Deionized water | q.s. to 1 liter |

-continued

| Ingredient | Amount |
| --- | --- |
| (initial pH 6.1) | |

*V-8 Juice, Campbell Soup Co., Camden N.J.
**Meer Corp.

The slant is inoculated with *Aspergillus nidulans* var. *roseus* NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
| --- | --- |
| Sucrose | 25 g |
| Blackstrap molasses | 36 g |
| Corn-steep liquor | 6 g |
| Malt extract | 10 g |
| $K_2HPO_4$ | 2 g |
| Enzymatic hydrolysate of casein* | 10 g |
| Tap water | 1100 ml |
| (initial pH 6.5–6.7) | |

*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows: The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM V | |
| --- | --- |
| Ingredient | Amount |
| $ZnSO_4 \cdot 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 \cdot 7H_2O$ | 5.5 g/L |
| $FeSO_4 \cdot 7H_2O$ | 0.1 g/L |
| Cottonseed oil | 40.0 ml |
| (Antifoam)**** | 1.0 ml |
| Tap water | 1000.0 ml |
| (initial pH 6.8–7.0) | |

*O.M. Peptone, Amber Laboratories, Juneau, Wisc.
**Stadex 11, A.E. Staley Co., Decatur, Ill.
***N-Z-Amine A, Humko Sheffield Chemical, Lyndhurst, N.J.
****P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| $K_2HPO_4$ | 2 g |
| Tap water | 1000 ml |
| (initial pH 6.1) | |

*N-Z-Case

EXAMPLE 13

Separation of the A-42355 Antibiotic Complex

Whole fermentation broth (4127 liters), obtained by the method described in Example 12 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 14

Isolation of A-30912 Factor H

A-42355 antibiotic complex (5.0 g), prepared as described in Example 13, was dissolved in 35 ml of methanol:water:acetonitrile (7:2:1); the resulting solution was filtered and introduced onto a 3.7-cm I.D.×42-cm glass column (Michel-Miller Column) through a loop with the aid of a valve system. The column was packed with LP-1/$C_{18}$ silica gel reversed phase resin (10–20 microns) in methanol:water:acetonitrile (7:2:1) as described in Example 15. The solvent was moved through the column at a flow rate of 13 ml/min at ca. 120 psi, using an F.M.I. pump with valveless piston design and collecting one fraction every two minutes. Elution of the antibiotic was monitored by UV at 280 nm as described in Example 1, Sect. D. Fractions 112–132 were combined with fractions 106–117 from a second similar purification. The combined fractions were concentrated under vacuum to an oil. The oil was dissolved in a small volume of tert-butanol and lyophilized to give 173 mg of crude A-30912 factor H.

The crude A-30912 factor H (150 mg) was dissolved in 8 ml of methanol:water:acetonitrile (7:2:1); the resulting solution was filtered and introduced onto a 2.0-cm I.D.×32-cm glass column, as described above. The solvent was moved through the column at a flow rate of 8 ml/min at ca. 80 psi collecting one fraction every three minutes. Elution of the antibiotic was monitored at 280 nm. Fractions 17 and 18 were combined and concentrated under vacuum to give an oil. The oil was dissolved in a small volume of tert-butanol and lyophilized to give 29 mg of A-30912 factor H.

EXAMPLE 15

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16-20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 16

Slurry Packing Procedure for Michel-Miller Columns

General Information

A. Analytical or preparative columns can be packed by this procedure.

B. Silica gels and silica gel reversed phase packings (e.g., Quantum LP-1, particle size 10–20 microns; Li-Chroprep RP-8 and RP-18, particle size 25–40 microns) are recommended. However, other silica gels (e.g., Shandons ODS Hypersil, particle size 5 microns) as well as other types of resins have been packed successfully by this procedure.

C. Generally, a pressure of less than 200 psi and flow rates between 5–40 ml/minute are required for this slurry packing technique; this is dependent on column volume and size. PLEASE NOTE: Packing pressure should exceed pressure used during actual separation by 30–50 psi; this will assure no further compression of the adsorbent during separation runs. Columns packed by this procedure with reversed-phase silica gel can be operated for several years without loss of efficiency.

D. Sudden decrease in pressure may cause cracks or channels to form in the packing material, which would greatly reduce column efficiency. Therefore, it is important to let the pressure drop slowly to zero whenever the pump has been turned off.

E. Approximate volume of columns (Ace Glass Cat. No., unpacked): 5795-04, 12 ml; 5795-10, 110 ml; 5795-16, 300 ml; 5795-24, 635 ml; and 5796-34, 34 ml.

F. The time required to pack a glass column will vary from minutes to several hours depending on column size and experience of the scientist.

Example

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. NOTE: The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solventdelivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure.

NOTE: Always allow pressure to decrease slowly after turning off pump—this will prevent formation of any cracks or channels in the packing material.

10. Relieve pressure and disconnect precolumn carefully. With small spatula remove a few mm (2-4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 17

Preparation of Tetrahydro-A-30912H

A-30912 factor H is dissolved in ethanol. $PtO_2$ in absolute ethanol is reduced to form Pt, which in turn is used to reduce the A-30912 factor H catalytically, using hydrogenation under positive pressure until the reaction is complete (about 2-3 hours). The reaction mixture is filtered and concentrated under vacuum. The residue is dissolved in a small amount of tert-butanol and lyophilized to give tetrahydro-A-30912H.

EXAMPLE 18

The following procedure, which gives the preparation of the compound of formula 3 wherein $R^1$ is $CH_3(CH_2)_{11}-$, illustrates preparation of the compounds of formula 3, using the "active ester" method.

n-Tridecanoyl Derivative of A-30912H Nucleus

A. Preparation of 2,4,5-Trichlorophenyl n-Tridecanoate

A solution of n-tridecanoic acid (Sigma Chemical Co.) (12.5 g), 2,4,5-trichlorophenol (11.5 g), and N,N'-dicyclohexylcarbodiimide (12.0 g) in methylene chloride (650 ml) is stirred at room temperature for 16 hours. The reaction mixture is then filtered and dried in vacuo to give 2,4,5-trichlorophenyl n-tridecanoate (22 g). The material is purified by column chromatography over silica gel (Woelm) using toluene as the eluent. Fractions are monitored by TLC using a shortwave UV light for detection. Fractions containing the purified product are pooled and concentrated in vacuo to dryness.

B. Acylation of A-30912H Nucleus with 2,4,5-Trichlorophenyl-n-Tridecanoate

A solution of 2,4,5-trichlorophenyl n-tridecanoate (3.3 mmoles) and A-30912H nucleus (1 mmole) in dimethylformamide (DMF) (200 ml) is stirred at room temperature for 16 hours. Removal of solvent in vacuo affords a residue. The residue is slurried with methylene chloride (300 ml) for 45 minutes, and the mixture is filtered. The filtrate is discarded. The remaining solids are extracted with methanol (300 ml), and the methanol extract is filtered and concentrated in vacuo to give a crude product.

The crude product is purified by reversed-phase HPLC as follows:

A sample of the crude product (1 g), dissolved in methanol (5 ml), is injected into a 1-×32-inch stainless steel column packed with LP-1/$C_{18}$ resin (see Examples 15 and 16). The column is eluted with a solvent system comprising 3:3:4 $H_2O/CH_3OH/CH_3CN$. The elution is performed at a pressure of 1000–1500 psi with a flow rate of 11–12 ml/min using an LDC duplex pump (Milton-Roy). The effluent is monitored by a UV detector (ISCO-UA-5) at 280 nm. Fractions are collected every two minutes (21–24 ml). The fractions containing the desired product are pooled and dried in vacuo to afford the title product. The purified product is analyzed by TLC using reversed-phase $C_{18}$ plates (Whatman $KC_{18}$) and a solvent system comprising 1:2:2 (v/v) $H_2O/CH_3OH/CH_3CN$. After development, the plates are observed under UV light to detect the product.

EXAMPLE 19

The following procedure, which gives the preparation of the compound of formula 4 wherein $R^1$ is N-(n-dodecanoyl)-p-aminobenzoyl, illustrates the method of preparation of the Debono I compounds of formula 4.

N-(n-Dodecanoyl)-p-aminobenzoyl Derivative of A-30912H Nucleus

A. Preparation of N-(n-Dodecanoyl)-p-aminobenzoic Acid n-Dodecanoyl chloride (8.74 g; 40 mmoles) is added dropwise to a solution of p-aminobenzoic acid (40 mmoles) dissolved in pyridine (100 ml). The mixture is stirred for 3 hours and poured into water (3 L). The precipitate which forms is filtered and dried in vacuo to give N-(n-dodecanoyl)-p-aminobenzoic acid (11.01 g).

B. Preparation of the 2,4,5-Trichlorophenyl Ester of N-(n-Dodecanoyl)-p-aminobenzoic Acid N-(n-Dodecanoyl)-p-aminobenzoic acid (11.01 g; 34.5 mmoles), 2,4,5-trichlorophenol (7.5 g; 38 mmoles), and N,N'-dicyclohexylcarbodiimide (6.94 g; 34.5 mmoles) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g).

C. Acylation of A-30912H Nucleus

A-30912H nucleus (10.2 mmoles) and the 2,4,5-trichlorophenyl ester of N-(n-dodecanoyl)-p-aminobenzoic acid (10.2 mmoles) are dissolved in dimethylformamide (100 ml). The solution is stirred at room temperature for 15 hours. Solvent is removed in vacuo to give a residue which is washed twice with diethyl ether. The washes are discarded. The washed residue is dissolved in methanol (50 ml) and is purified by reversed phase HPLC by means of a "Prep LC/System 500" unit (Waters Associates, Inc., Milford, Massachusetts) using a Prep Pak-500/C18 column (Water Associates, Inc.) as the stationary phase. The column is eluted isocratically with H$_2$O/CH$_3$OH/CH$_3$CN (25:65:10 v/v) at 500 psi. The fractions are analyzed by TLC using silica gel plates and H$_2$O/CH$_3$OH/CH$_3$CN (25:65:10 v/v) as the solvent system. Fractions containing the desired product are combined and lyophilized to give the N-(n-dodecanoyl)-p-aminobenzoyl derivative of A-30912H nucleus.

EXAMPLE 20

The following procedure, which gives the preparation of the compound of formula 4 wherein R$^1$ is p-(n-octyloxy)benzoyl, illustrates the method of preparation of the Debono II compounds of formula 4.

p-(n-Octyloxy)benzoyl Derivative of A-30912H Nucleus

A. Preparation of p-(n-Octyloxy)benzoic Acid

A solution of p-hydroxybenzoic acid (19.2 g, 150 moles) in 10% aqueous sodium hydroxide (120 ml) is added to dimethyl sulfoxide (DMSO) (480 ml) previously heated to 80° C. n-Octyl bromide (28.95 g, 150 moles) is added dropwise to the solution. The reaction mixture is stirred for 4 hours at room temperature after which it is poured into ice water (1200 ml). Conc. hydrochloric acid (30 ml) is added, and the mixture is allowed to stand until precipitation is complete. The precipitate is collected, dried, and crystallized from acetonitrile-water. mp 97°–99° C.

Analysis for C$_{15}$H$_{22}$O$_3$: Calculated: C, 71.97; H, 8.86; Found: C, 71.72, H, 9.10.

B. Preparation of the 2,4,5-Trichlorophenyl Ester of p-(n-Octyloxy)benzoic Acid p-(n-Octyloxy)benzoic acid (6.18 g, 24.7 mmoles), 2,4,5-trichlorophenol (5.39 g, 27.2 mmoles) and N,N'-dicyclohexylcarbodiimide (4.94 g, 24.7 mmoles) are dissolved in methylene chloride (200 ml). The mixture is stirred at room temperature for 18 hours and then is filtered. The filtrate is evaporated to give an oil, which is crystallized from CH$_3$CN-H$_2$O to give the 2,4,5-trichlorophenyl ester of p-(n-octyloxy)benzoic acid.

NMR Analysis: δ4.02 (2H, t, J=3Hz), δ7.0 (1H, d, J=4Hz), 7.23 (s, 1H), 7.3 (s, 1H), 8.08 (d, 1H, J=4Hz).

C. Acylation of A-30912H Nucleus

A-30912H nucleus (17.8 mmoles) and the 2,4,5-trichlorophenyl ester of p-(n-octyloxy)benzoic acid (35.7 mmoles) are dissolved in dimethylformamide (150 ml). The solution is stirred at room temperature for 16–20 hours. Solvent is removed in vacuo, and the residue is washed twice with diethyl ether and twice with methylene chloride. The washes are discarded. The washed residue is dissolved in ethyl acetate:methanol (1:3) (80 ml) and is purified by HPLC using a "Prep LC/System 500" unit, using silica gel as the stationary phase. The column is eluted stepwise with methanol:ethyl acetate (1:4 to 2:3) solvent systems. The fractions are analyzed by TLC using silica gel (Merck) and ethyl acetate:methanol (3:2 v/v) as the solvent system. Fractions devoid of A-30912H nucleus are pooled and lyophilized to give the p-(n-octyloxy)benzoyl derivative of A-30912H nucleus.

EXAMPLES 21–23

The compound of formula 3 wherein R is n-propyl and R$^1$ is n-tridecyl, prepared according to the procedure of Example 18, but using as a starting material the compound of formula 1 wherein R is n-propyl (prepared by the method of Example 5).

The compound of formula 4 wherein R is isobutyl and R$^1$ is N-(n-dodecanoyl)-p-aminobenzoyl, prepared according to the procedure of Example 19, but using as a starting material the compound of formula 1 wherein R is isobutyl (prepared by the method of Example 6).

The compound of formula 4 wherein R is n-hexyl and R$^1$ is p-(n-octyloxy)benzoyl, prepared according to the procedure of Example 20, but using as a starting material the compound of formula 1 wherein R is n-hexyl (prepared by the method of Example 8).

We claim:
1. A-30912H-type compounds of the formula

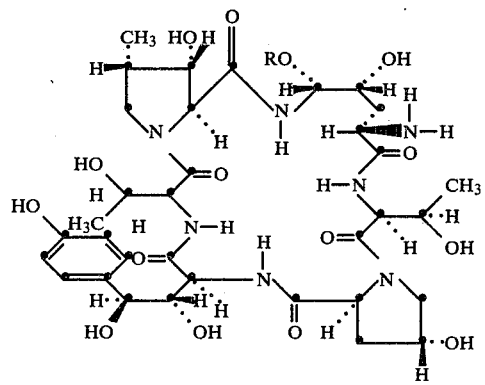

wherein R is C$_1$–C$_6$ alkyl and the acid addition salts thereof.

2. The compound of claim 1 wherein R is methyl and the acid addition salts thereof.

3. The compound of claim 2 wherein R is methyl.

4. The compound of claim 1 wherein R is ethyl and the acid addition salts thereof.

5. The compound of claim 4 wherein R is ethyl.

6. The compound of claim 1 wherein R is n-propyl and the acid addition salts thereof.

7. The compound of claim 6 wherein R is n-propyl.

8. The compound of claim 1 wherein R is isopropyl and the acid addition salts thereof.

9. The compound of claim 1 wherein R is n-butyl and the acid addition salts thereof.

10. The compound of claim 1 wherein R is isobutyl and the acid addition salts thereof.

11. The compound of claim 1 wherein R is tert-butyl and the acid addition salts thereof.

12. The compound of claim 1 wherein R is n-pentyl and the acid addition salts thereof.

13. The compound of claim 1 wherein R is n-hexyl and the acid addition salts thereof.

14. The compound of claim 1 wherein R is 2-ethyl-1-butyl and the acid addition salts thereof.

15. The compound of claim 1 wherein R is 3-methyl-1-butyl and the acid addition salts thereof.

16. The method of deacylating an antibiotic having the following structure:

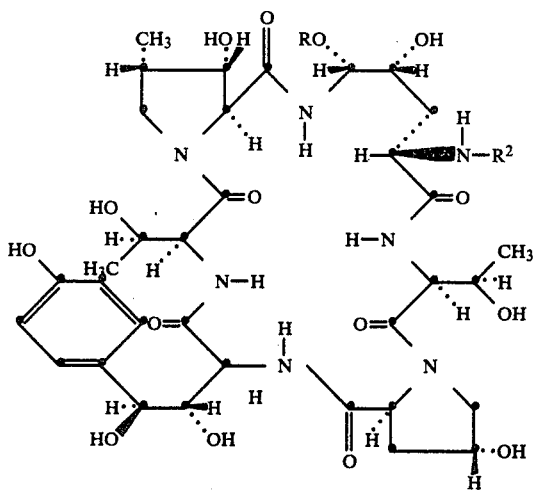

wherein R is $C_1$–$C_6$ alkyl and $R^2$ is linoleoyl or stearoyl which comprises exposing the antibiotic in an aqueous medium to an enzyme which deacylates and which is produced by a microorganism of the family Actinoplanaceae until substantial deacylation is accomplished.

17. The method of claim 16 wherein the microorganism of the family Actinoplanaceae is a member of the genus Actinoplanes.

18. The method of claim 17 wherein the microorganism is *Actinoplanes utahensis*.

19. The method of claim 18 wherein the microorganism is *A. utahensis* NRRL 12052 or a mutant thereof which produces the enzyme.

20. The method of claim 19 wherein the microorganism is *A. utahensis* NRRL 12052.

21. The method of claim 16 wherein the microorganism is *Streptosporangium roseum* var. *hollandensis* NRRL 12064, or a mutant thereof which produces the enzyme.

22. The method of claim 21 wherein the microorganism is *Streptosporangium roseum* var. *hollandensis* NRRL 12064.

23. The method of claim 17 wherein the microorganism is *Actinoplanes missouriensis* NRRL 12053 or a mutant thereof which produces the enzyme.

24. The method of claim 23 wherein the microorganism is *Actinoplanes missouriensis* NRRL 12053.

25. The method of claim 17 wherein the microorganism is Actinoplanes sp. NRRL 12065 or a mutant thereof which produces the enzyme.

26. The method of claim 25 wherein the microorganism is Actinoplanes sp. NRRL 12065.

27. The method of claim 17 wherein the microorganism is Actinoplanes sp. NRRL 8122 or a mutant thereof which produces the enzyme.

28. The method of claim 27 wherein the microorganism is Actinoplanes sp. NRRL 8122.

29. A method of claims 16, 17, 18, 19, 20, 21, 22, 23, 24, 25, 26, 27 or 28 wherein the enzyme is present in a culture of the producing Actinoplanaceae microorganism.

30. A method of claims 16, 17, 18, 19, 20, 21, 22, 23, 24, 25, 26, 27 or 28 wherein the antibiotic has the structure in which R is methyl and $R^2$ is linoleoyl.

31. A method of claims 16, 17, 18, 19 or 20 wherein the antibiotic has the structure in which R is methyl and $R^2$ is stearoyl.

32. A method of claim 29 wherein the antibiotic has the structure in which R is methyl and $R^2$ is linoleoyl.

33. A method of claim 29 wherein the antibiotic has the structure in which R is methyl and $R^2$ is stearoyl.

* * * * *